(12) United States Patent
Sharma

(10) Patent No.: US 12,004,848 B2
(45) Date of Patent: Jun. 11, 2024

(54) BLOOD FLOW METER

(71) Applicant: Boston Scientific Limited, Hamilton (BM)

(72) Inventor: Deepak Kumar Sharma, Muzaffarnafar (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 685 days.

(21) Appl. No.: 16/672,562

(22) Filed: Nov. 4, 2019

(65) Prior Publication Data

US 2020/0138301 A1 May 7, 2020

Related U.S. Application Data

(60) Provisional application No. 62/755,128, filed on Nov. 2, 2018.

(51) Int. Cl.
*A61B 5/027* (2006.01)
*A61B 5/0215* (2006.01)

(52) U.S. Cl.
CPC .......... *A61B 5/027* (2013.01); *A61B 5/02158* (2013.01)

(58) Field of Classification Search
CPC .............................. A61B 5/027; A61B 5/02158
See application file for complete search history.

(56) References Cited

U.S. PATENT DOCUMENTS

| | | | |
|---|---|---|---|
| 4,957,504 A | 9/1990 | Chardack | |
| 5,527,159 A | 6/1996 | Bozeman, Jr. et al. | |
| 5,964,694 A | 10/1999 | Siess et al. | |
| 6,007,478 A | 12/1999 | Siess et al. | |
| 6,176,822 B1 | 1/2001 | Nix et al. | |
| 6,176,848 B1 | 1/2001 | Rau et al. | |
| 7,010,954 B2 | 3/2006 | Siess et al. | |
| 9,474,840 B2 | 10/2016 | Siess | |
| 9,669,142 B2 | 6/2017 | Spanier et al. | |
| 10,765,791 B2 | 9/2020 | Moyer et al. | |
| 10,864,308 B2 | 12/2020 | Muller et al. | |
| 10,960,118 B2 | 3/2021 | Sunagawa | |
| 11,027,114 B2 | 6/2021 | D'Ambrosio et al. | |
| 11,033,727 B2 | 6/2021 | Tuval et al. | |
| 11,529,062 B2 | 12/2022 | Moyer et al. | |

(Continued)

FOREIGN PATENT DOCUMENTS

| | | | | |
|---|---|---|---|---|
| CN | 110049792 | * | 11/2017 | .......... A61M 60/205 |
| CN | 110049792 B | | 1/2022 | |

(Continued)

*Primary Examiner* — Rochelle D Turchen

(74) *Attorney, Agent, or Firm* — Seager, Tufte & Wickhem LLP

(57) ABSTRACT

A blood flow meter includes a rotor configured to be placed within a flow of blood and to be driven to rotate by the flow of blood; a magnetic encoder configured to sense the rotation of the rotor and to generate a rotation signal based on the sensed rotation of the rotor; a first pressure sensor configured to measure an upstream pressure; a second pressure sensor configured to measure a downstream pressure; and a control unit. The control unit is configured to determine a differential pressure, the differential pressure including a difference between the downstream pressure and the upstream pressure; and cause an alteration to the rotation of the rotor based on the differential pressure.

9 Claims, 3 Drawing Sheets

(56) References Cited

U.S. PATENT DOCUMENTS

| | | |
|---|---|---|
| 2004/0191116 A1 | 9/2004 | Jarvik et al. |
| 2005/0267322 A1 | 12/2005 | LaRose |
| 2017/0128646 A1 | 5/2017 | Karch |
| 2019/0053714 A1* | 2/2019 | Guelen .............. A61B 5/02225 |
| 2020/0306432 A1* | 10/2020 | Pekkan ............... A61M 60/857 |
| 2021/0322757 A1 | 10/2021 | D'Ambrosio et al. |
| 2022/0167862 A1 | 6/2022 | Edelman et al. |

FOREIGN PATENT DOCUMENTS

| | | | |
|---|---|---|---|
| WO | 2011039091 A1 | 4/2011 | |
| WO | 2014043650 A2 | 3/2014 | |
| WO | WO-2014043650 A2 * | 3/2014 | ........... A61B 10/007 |
| WO | 2018096531 A1 | 5/2018 | |
| WO | WO-2018096531 A1 * | 5/2018 | ........... A61M 1/101 |

* cited by examiner

BLOOD FLOW METER

This application claims priority to Provisional Application No. 62/755,128, filed Nov. 2, 2018, which is herein incorporated by reference in its entirety.

TECHNICAL FIELD

The present disclosure relates to blood flow meters. More specifically, the disclosure relates to blood flow meters configured to maintain a zero slip condition.

BACKGROUND

Blood flow meters are used to monitor the blood flow in blood vessels and to measure cardiac output. Blood flow is an important physiological parameter and one that is often difficult to measure. The average velocities of blood flow vary over a wide range depending on the diameter of the blood vessel and other factors. Blood flow meters may be used for inspection of blocks in blood flow, testing artificial blood vessels during organ transplantation, monitoring during fistula creation in dialysis, and/or the like. Common blood flow meters include electromagnetic blood flow meters, ultrasonic blood flow meters, NMR blood flow meters, laser Doppler blood flow meters, and/or the like. Many of these common meters are only capable of measurement of very low blood flow rates, and many are quite expensive to make and operate.

SUMMARY

In an Example 1, a blood flow meter, comprising: a rotor configured to be placed within a flow of blood and to be driven to rotate by the flow of blood; a magnetic encoder configured to sense the rotation of the rotor and to generate a rotation signal based on the sensed rotation of the rotor; a first pressure sensor configured to measure an upstream pressure, wherein the upstream pressure is the blood pressure upstream of the rotor; a second pressure sensor configured to measure a downstream pressure, wherein the downstream pressure is the blood pressure downstream of the rotor; and a control unit configured to: determine a differential pressure, the differential pressure comprising a difference between the downstream pressure and the upstream pressure; and cause an alteration to the rotation of the rotor based on the differential pressure.

In an Example 2, the blood flow meter of Example 1, the control unit comprising a differential transducer operatively coupled to the first and second sensors, and configured to determine the differential pressure.

In an Example 3, the blood flow meter of either of Examples 1 or 2, further comprising a motor configured to provide external energy to the rotor, thereby causing the alteration to the rotation of the rotor.

In an Example 4, the blood flow meter of Example 3, wherein the motor is a stepper motor.

In an Example 5, the blood flow meter of either of Examples 3 or 4, wherein the control unit comprises a controller configured to provide a control signal to the motor to control the motor.

In an Example 6, the blood flow meter of any of Examples 1-5, wherein the control unit is configured to cause the alteration to the rotation of the rotor in response to determining that the differential pressure is not zero.

In an Example 7, the blood flow meter of any of Examples 1-6, wherein the control unit is further configured to determine, based on the rotation signal, a blood flow rate.

In an Example 8, a method of using a blood flow meter having a rotor placed in the flow of blood to determine a blood flow rate, wherein the rotor is configured to be driven to rotate by the flow of blood, the method comprising: measuring, using an upstream pressure sensor, an upstream pressure, wherein the upstream pressure is the blood pressure upstream of the rotor; measuring, using a downstream pressure sensor, a downstream pressure, wherein the downstream pressure is the blood pressure downstream of the rotor; determining a differential pressure, the differential pressure comprising a difference between the downstream pressure and the upstream pressure; causing an alteration to the rotation of the rotor based on the differential pressure; sensing, using a magnetic encoder, the rotation of the rotor; generating, using the magnetic encoder and based on the rotation of the rotor, a rotation signal; and determining, based on the rotation signal, a blood flow rate.

In an Example 9, the method of Example 8, wherein the step of determining the differential pressure is performed using a differential transducer.

In an Example 10, the method of either of Examples 8 or 9, the blood flow meter comprising a motor configured to provide external energy to the rotor, thereby causing the alteration to the rotation of the rotor.

In an Example 11, the method of Example 10, wherein the motor is a stepper motor.

In an Example 12, the method of either of Examples 10 or 11, the blood flow meter comprising a controller, the method further comprising providing, using the controller, a control signal to the motor to control the motor.

In an Example 13, the method of any of Examples 8-12, further comprising determining that the differential pressure is not zero, wherein the step of causing the alteration to the rotation of the rotor is performed in response to determining that the differential pressure is not zero.

In an Example 14, a blood flow meter, comprising: a rotor configured to be placed within a flow of blood and to be driven to rotate by the flow of blood; a magnetic encoder configured to sense the rotation of the rotor and to generate a rotation signal based on the sensed rotation of the rotor; a first pressure sensor configured to measure an upstream pressure, wherein the upstream pressure is the blood pressure upstream of the rotor; a second pressure sensor configured to measure a downstream pressure, wherein the downstream pressure is the blood pressure downstream of the rotor; and a control unit configured to: determine a differential pressure, the differential pressure comprising a difference between the downstream pressure and the upstream pressure; and cause an alteration to the rotation of the rotor based on the differential pressure.

In an Example 15, the blood flow meter of Example 14, the control unit comprising a differential transducer operatively coupled to the first and second sensors, and configured to determine the differential pressure.

In an Example 16, the blood flow meter of Example 14, further comprising a motor configured to provide external energy to the rotor, thereby causing the alteration to the rotation of the rotor.

In an Example 17, the blood flow meter of Example 16, wherein the motor is a stepper motor.

In an Example 18, the blood flow meter of Example 16, wherein the control unit comprises a controller configured to provide a control signal to the motor to control the motor.

In an Example 19, the blood flow meter of Example 14, wherein the control unit is configured to cause the alteration to the rotation of the rotor in response to determining that the differential pressure is not zero.

In an Example 20, the blood flow meter of Example 14, wherein the control unit is further configured to determine, based on the rotation signal, a blood flow rate.

In an Example 21, a method of using a blood flow meter having a rotor placed in the flow of blood to determine a blood flow rate, wherein the rotor is configured to be driven to rotate by the flow of blood, the method comprising: measuring, using an upstream pressure sensor, an upstream pressure, wherein the upstream pressure is the blood pressure upstream of the rotor; measuring, using a downstream pressure sensor, a downstream pressure, wherein the downstream pressure is the blood pressure downstream of the rotor; determining a differential pressure, the differential pressure comprising a difference between the downstream pressure and the upstream pressure; causing an alteration to the rotation of the rotor based on the differential pressure; sensing, using a magnetic encoder, the rotation of the rotor; generating, using the magnetic encoder and based on the rotation of the rotor, a rotation signal; and determining, based on the rotation signal, a blood flow rate.

In an Example 22, the method of Example 21, wherein the step of determining the differential pressure is performed using a differential transducer.

In an Example 23, the method of Example 21, the blood flow meter comprising a motor configured to provide external energy to the rotor, thereby causing the alteration to the rotation of the rotor.

In an Example 24, the method of Example 23, wherein the motor is a stepper motor.

In an Example 25, the method of Example 23, the blood flow meter comprising a controller, the method further comprising providing, using the controller, a control signal to the motor to control the motor.

In an Example 26, the method of Example 21, further comprising determining that the differential pressure is not zero, wherein the step of causing the alteration to the rotation of the rotor is performed in response to determining that the differential pressure is not zero.

In an Example 27, a blood flow meter, comprising: a rotor configured to be placed within a flow of blood and to be driven to rotate by the flow of blood; a magnetic encoder configured to sense the rotation of the rotor and to generate a rotation signal based on the sensed rotation of the rotor; a first pressure sensor configured to measure an upstream pressure, wherein the upstream pressure is the blood pressure upstream of the rotor; a second pressure sensor configured to measure a downstream pressure, wherein the downstream pressure is the blood pressure downstream of the rotor; a differential transducer configured to determine a differential pressure, the differential pressure comprising a difference between the downstream pressure and the upstream pressure; and a controller configured to cause an alteration to the rotation of the rotor based on the differential pressure.

In an Example 28, the blood flow meter of Example 27, further comprising a motor configured to provide external energy to the rotor, thereby causing the alteration to the rotation of the rotor.

In an Example 29, the blood flow meter of Example 28, wherein the motor is a stepper motor.

In an Example 30, the blood flow meter of Example 28, wherein the control unit comprises a controller configured to provide a control signal to the motor to control the motor.

In an Example 31, the blood flow meter of Example 27, wherein the control unit is configured to cause the alteration to the rotation of the rotor in response to determining that the differential pressure is not zero.

In an Example 32, the blood flow meter of Example 27, wherein the control unit is further configured to determine, based on the rotation signal, a blood flow rate.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
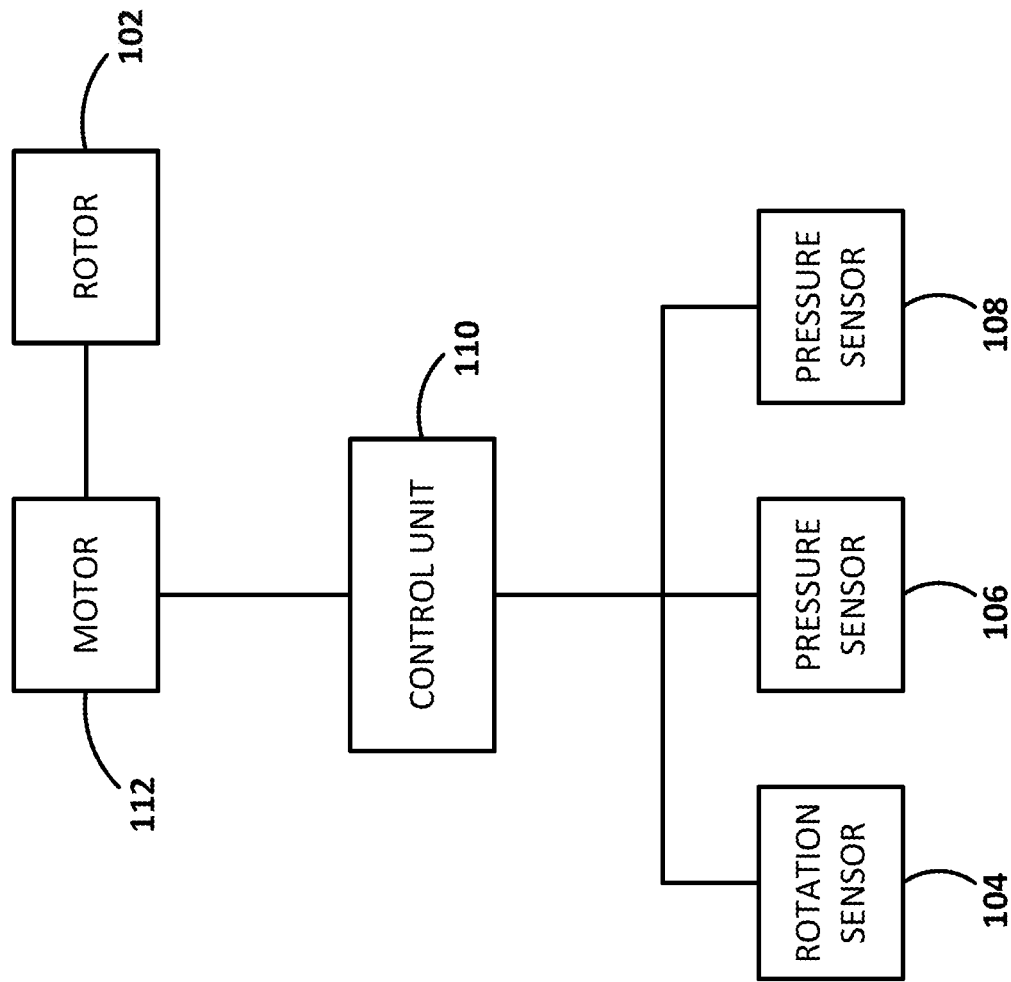
FIG. 1 is a block diagram depicting an illustrative blood flow meter, in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops;

machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

FIG. 1 is a block diagram depicting an illustrative blood flow meter 100, in accordance with embodiments of the subject matter disclosed herein. Embodiments of the illustrative blood flow meter 100 may be used in any number of different applications and may include any number of different configurations, constructions, and/or the like. According to embodiments, the blood flow meter 100 may be configured to be inserted into a blood conduit such as, for example, a blood vessel, an artificial blood vessel, a blood tube, and/or the like. In embodiments, the blood flow meter 100 may be coupled to a catheter. The blood flow meter 100 may be an independent device designed to be implanted in a patient, and may include anchors configured to facilitate holding the blood flow meter 100 in a particular position.

As shown, the blood flow meter 100 includes a rotor 102 configured to be placed within a flow of blood and to be driven to rotate by the flow of blood. According to embodiments, the rotor 102 may be rotatably mounted on a shaft using a bearing so that the rotor may be able to rotate in response to blood flowing over the blades of the rotor 102. The rotor 102 may be of any size or shape suitable for the implementation for which the meter 100 is intended. For example, the rotor may be, or include, an impeller configured to rotate about one or more bearings.

The blood flow meter 100 includes a rotation sensor 104 configured to sense the rotation of the rotor 102. The rotation sensor 104 may be any type of sensing device capable of sensing a rotation of a rotor. The control unit 110 (described below) may be configured to determine, based on the rotation signal, a blood flow rate. In embodiments, the rotation sensor 104 may include a magnetic encoder disposed outside of the flow of blood, a sensor integrated into the rotor housing and/or bearing, a sensor integrated into a housing of the motor 112 (discussed below), and/or the like. The rotation sensor 104 may be configured to generate a rotation signal based on the sensed rotation of the rotor 102. The rotation signal may include, for example, a series of magnetic impulse measurements representative of an alteration of a magnetic field caused by the passing of each blade of an impeller through the field.

The blood flow meter 100 also includes a first pressure sensor 106 configured to measure an upstream pressure, and a second pressure sensor 108 configured to measure a downstream pressure. According to embodiments, the upstream pressure is a blood pressure upstream of the rotor, and a downstream pressure is a pressure downstream of the rotor. As the term is used herein, "upstream" of a specified location refers to a region within the blood conduit that includes blood, flowing in the blood flow direction, that has not yet reached the specified location. Conversely, the term "downstream" refers to a region within the blood conduit that includes blood, flowing in the blood flow direction, that has already reached, and passed, the specified location. The pressure sensors 106 and 108 may include any number of different types of pressure sensors such as, for example, piezoelectric sensors, capacitive sensors, optical sensors, and/or the like.

The blood flow meter 100 further includes a control unit 110. The control unit 110 may be any type of control device. In embodiments, the control unit 110 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the control unit 110 may include a processing unit configured to communicate with memory to execute computer-executable instructions stored in the memory. Although the control unit 110 is referred to herein in the singular, the control unit 110 may be implemented in multiple instances, distributed across multiple computing devices, instantiated within multiple virtual machines, and/or the like.

The control unit 110 may also be configured to store information in a memory (not shown) and/or access information from the memory. The control unit 110 may execute instructions and perform desired tasks as specified by computer-executable instructions stored in the memory. In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

According to embodiments, the control unit is configured to determine a differential pressure. The differential pressure is a difference between the downstream pressure and the upstream pressure. According to embodiments, the differential pressure may be determined using any number of various methods by the control unit. In embodiments, the control unit 110 includes a differential transducer operatively coupled to the first and second sensors, and configured to determine the differential pressure. in other embodiments, the control unit 110 may determine the differential pressure using a controller such as, for example, a microprocessor, or other hardware, software, and/or firmware technology.

According to embodiments, the control unit 110 may be configured to cause an alteration to the rotation of the rotor 102 based on the differential pressure. The control unit 110 may, for example, provide a control signal to a motor 112 that is configured to provide external energy to the rotor 102, thereby causing the alteration to the rotation of the rotor 102. For example, in embodiments in which the control unit 110 includes a differential pressure transducer, the control unit 110 may also include a controller configured to provide a control signal to the motor 112 to control the motor 112. In embodiments, the motor may be a stepper motor, a magnetic flux motor, and/or the like.

According to embodiments, the control unit 110 is configured to control the motor 112 so as to maintain a differential pressure of zero, or at least approximately zero. In this manner, the control unit 110 can control the motor 112 to maintain a zero slip condition based on the differential pressure. During operation of the blood flow meter 100, as the rotor 102 begins turning due to blood flow, drag forces, friction in the bearing and the inside of the meter, and turbulence around the rotor 102 leads to slip, which can cause damage to blood cells, as well as reduce the accuracy of blood flow rate measurements.

For a more accurate blood flow rate measurement and to reduce damage to blood cells, the control unit 110 may be configured to control the motor 112 so that the blood flow meter 100 does not consume energy out of the system. This may be achieved, for example, by maintaining a zero slip condition, in which there is no interaction between the blood cells and the rotor 102. To do so, the control unit 110 may be configured to maintain a differential pressure of zero (or at least approximately zero) across the rotor. For example, the control unit 110 may be configured to cause the alteration to the rotation of the rotor 102 in response to determining that the differential pressure is not zero. In this manner, the head generated by the energy added to the rotor 102 via the motor 112 equals the losses due to drag forces, friction in the bearing and inside of the meter, and turbulence. According to embodiments, the differential pressure may be measured continually, continuously, and/or periodically to facilitate providing feedback to the control unit 110 to control the motor 112 to maintain the zero slip condition.

The illustrative blood flow meter 100 shown in FIG. 1 is not intended to suggest any limitation as to the scope of use or functionality of embodiments of the present disclosure. The illustrative blood flow meter 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
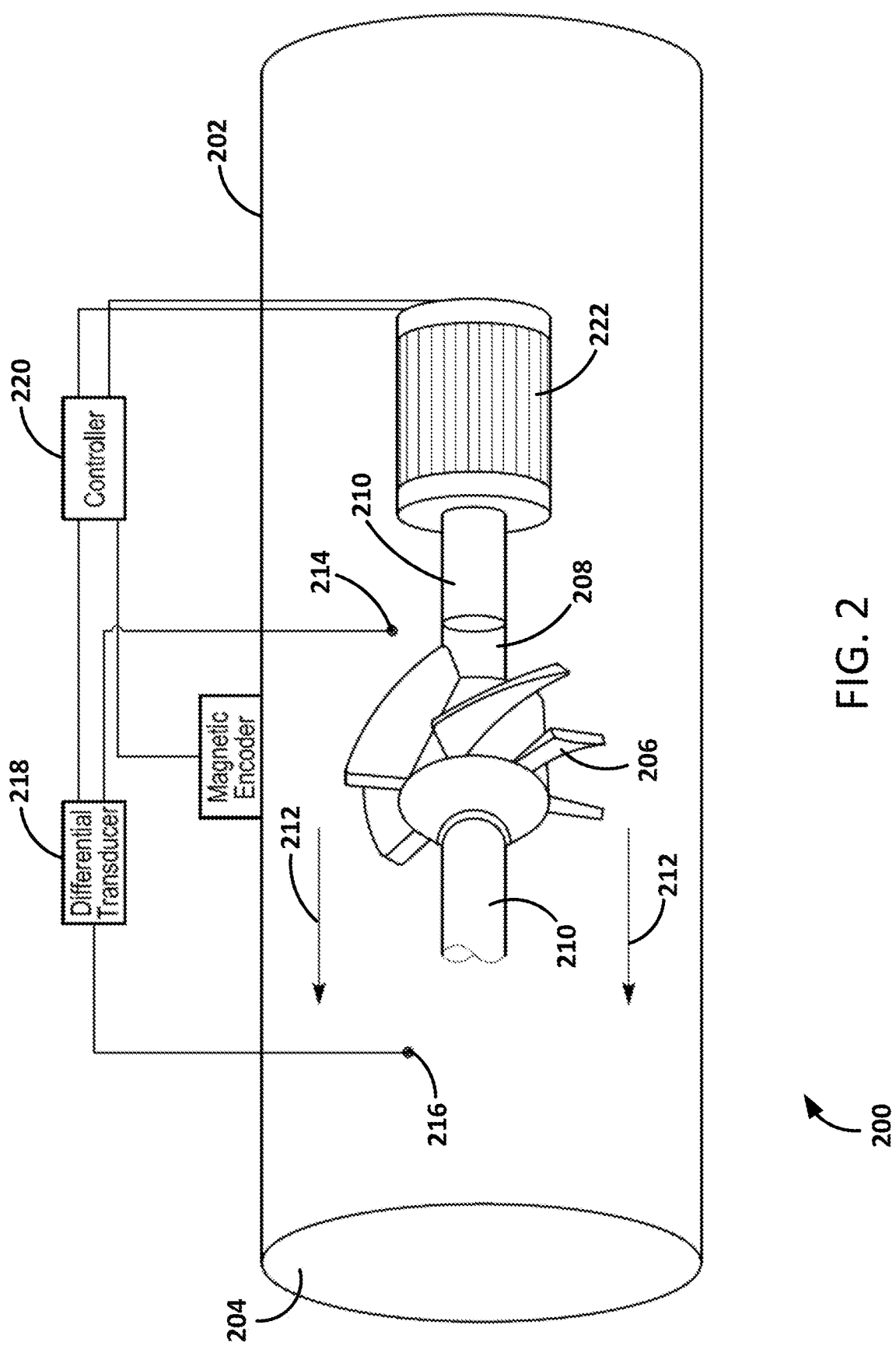
FIG. 2 is a schematic diagram depicting an illustrative blood flow meter, in accordance with embodiments of the subject matter disclosed herein.

FIG. 2 is a schematic diagram depicting an illustrative blood flow meter 200, in accordance with embodiments of the subject matter disclosed herein. According to embodiments, the blood flow meter 200 may be, be similar to, include, or be included in, the blood flow meter 100 depicted in FIG. 1. As shown in FIG. 2, the blood flow meter 200 may include a tube 202 partially enclosing a sensing chamber 204. A rotor 206 is disposed within the sensing chamber 204 and is rotatably mounted, via a bearing 208, to a shaft 210. The rotor 206 is configured to be placed within a flow of blood and to be driven to rotate by the flow of blood, the direction of which is indicated by arrows 212.

As shown, the illustrative blood flow meter 200 also includes a first pressure sensor 214, configured to measure an upstream pressure (a blood pressure upstream of the rotor 206), and a second pressure sensor 216, configured to measure a downstream pressure (a blood pressure downstream of the rotor). A differential transducer 218 is operatively coupled to the first and second pressure sensors and is configured to determine a differential pressure, which is a difference between the downstream pressure and the upstream pressure.

As shown in FIG. 2, the blood flow meter 200 further includes a controller 220 that is operatively coupled to the differential transducer 218 and is configured to cause an alteration to the rotation of the rotor 206, based on the differential pressure. In embodiments, the differential transducer 218 and the controller 220 may be integrated into a control unit. The controller 220 causes an alteration to the rotation of the rotor 206 by providing a control signal to a motor 222 that is operatively coupled to the rotor 206 and configured to add energy to the rotor 206 in response to receiving the control signal. The controller 220 also receives a rotation signal generated by a magnetic encoder 224, which is configured to sense the rotation of the rotor 206. Based on the rotation signal, the controller determines the blood flow rate.

The illustrative blood flow meter 200 shown in FIG. 2 is not intended to suggest any limitation as to the scope of use or functionality of embodiments of the present disclosure. The illustrative blood flow meter 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
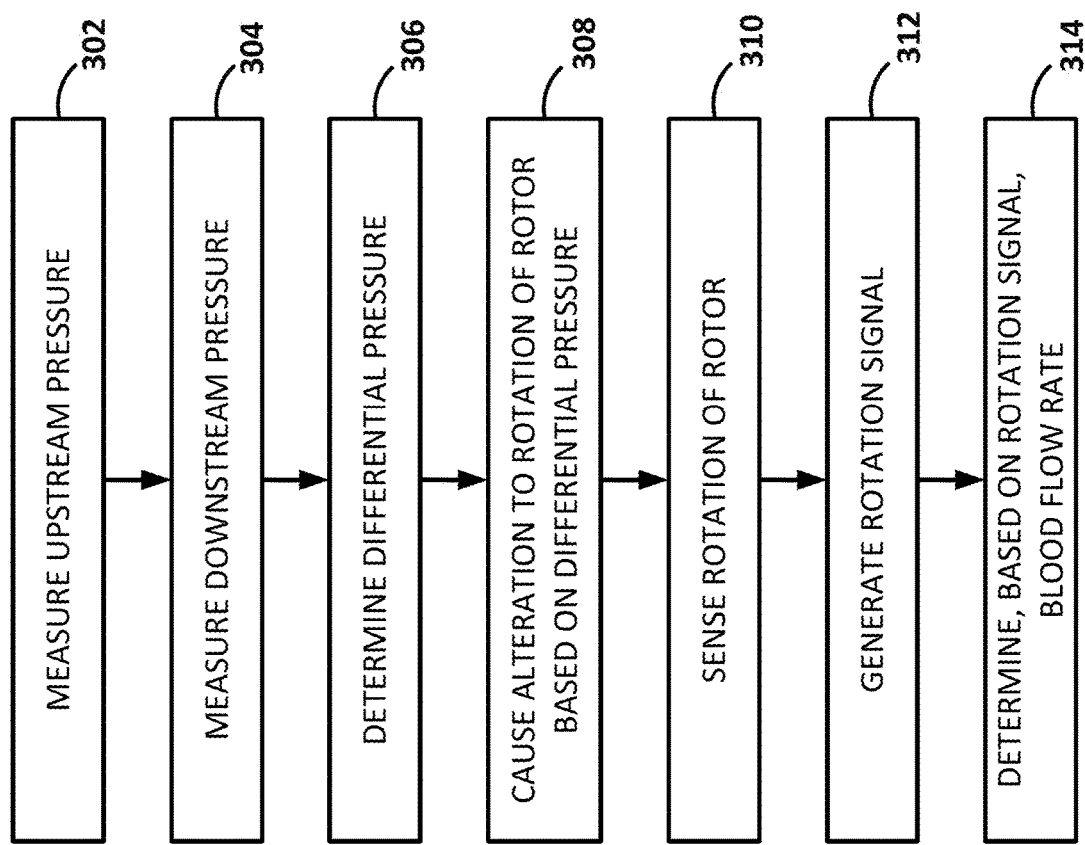
FIG. 3 is flow diagram depicting an illustrative method of using a blood flow meter having a rotor placed in the flow of blood to determine a blood flow rate, where the rotor is configured to be driven to rotate by the flow of blood, in accordance with embodiments of the subject matter disclosed herein.

FIG. 3 is flow diagram depicting an illustrative method 300 of using a blood flow meter having a rotor placed in the flow of blood to determine a blood flow rate, where the rotor is configured to be driven to rotate by the flow of blood. According to embodiments, the blood flow meter may be, be similar to, include, or be included in, the blood flow meter 100 depicted in FIG. 1 and/or the blood flow meter 200 depicted in FIG. 2. In embodiments, the method includes measuring, using an upstream pressure sensor, an upstream pressure, where the upstream pressure is the blood pressure upstream of the rotor (block 302), and measuring, using a downstream pressure sensor, a downstream pressure, where the downstream pressure is the blood pressure downstream of the rotor (block 304). The method further includes determining a differential pressure (block 306). The differential pressure is a difference between the downstream pressure and the upstream pressure, and may be determined by a controller, a differential transducer, and/or the like.

Embodiments of the method 300 further include causing an alteration to the rotation of the rotor based on the differential pressure (block 308). For example, the method 300 may include determining that the differential pressure is not zero, and where the step of causing the alteration to the rotation of the rotor is performed in response to determining that the differential pressure is not zero. The blood flow meter may include a motor configured to provide external energy to the rotor, thereby causing the alteration to the rotation of the rotor. The motor may be a magnetic flux motor, a stepper motor, and/or the like. A control unit (e.g., the control unit 110 depicted in FIG. 1 and/or the controller 220 depicted in FIG. 2) may be configured, for example, to provide a control signal to the motor to control the motor.

Embodiments of the method 300 further include sensing the rotation of the rotor (block 310). According to embodiments, the rotation of the rotor may be sensed using a rotation sensor such as, for example, a magnetic encoder. The rotation sensor generates a rotation signal (block 312), and a control unit determines, based on the rotation signal, the blood flow rate.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. A method of using a blood flow meter having a rotor placed in the flow of blood to determine a blood flow rate, the method comprising:
    initially permitting the rotor to rotate due to flow of blood over a plurality of blades of the rotor; and thereafter
    measuring, using an upstream pressure sensor, an upstream pressure, wherein the upstream pressure is the blood pressure upstream of the rotor;
    measuring, using a downstream pressure sensor, a downstream pressure, wherein the downstream pressure is the blood pressure downstream of the rotor;
    determining that a differential pressure is not zero, the differential pressure comprising a difference between the downstream pressure and the upstream pressure;
    causing an alteration to the rotation of the rotor in response to determining that the differential pressure is not zero;
    sensing, using a magnetic encoder, the rotation of the rotor;
    generating, using the magnetic encoder and based on the rotation of the rotor, a rotation signal; and
    determining, based on the rotation signal, the blood flow rate.

2. The method of claim 1, wherein the step of determining the differential pressure is performed using a differential transducer.

3. The method of claim 1, the blood flow meter comprising a motor configured to provide external energy to the rotor, thereby causing the alteration to the rotation of the rotor.

4. The method of claim 3, wherein the motor is a stepper motor.

5. The method of claim 3, the blood flow meter comprising a controller, the method further comprising providing, using the controller, a control signal to the motor to control the motor.

6. The method of claim 5, wherein determining the blood flow rate based on the rotation signal comprises using the controller to determine the blood flow rate.

7. The method of claim 5, wherein the controller is operatively coupled to the upstream pressure sensor and the downstream pressure sensor.

8. The method of claim 1, further comprising inserting the blood flow meter into a blood vessel before permitting the rotor to rotate due to the flow of blood over the plurality of blades of the rotor.

9. The method of claim 1, wherein causing the alteration to the rotation of the rotor in response to determining that the differential pressure is not zero comprises maintaining a zero slip condition based on the differential pressure.

\* \* \* \* \*